US011571274B2

(12) United States Patent
Wakazome et al.

(10) Patent No.: US 11,571,274 B2
(45) Date of Patent: Feb. 7, 2023

(54) DENTAL INSTRUMENT, CONTROL METHOD THEREOF, AND THREE-DIMENSIONAL MEASURING

(71) Applicant: J. MORITA MFG. CORP., Kyoto (JP)

(72) Inventors: Naonori Wakazome, Kyoto (JP); Mikinori Nishimura, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 384 days.

(21) Appl. No.: 16/822,947

(22) Filed: Mar. 18, 2020

(65) Prior Publication Data

US 2020/0297201 A1 Sep. 24, 2020

(30) Foreign Application Priority Data

Mar. 18, 2019 (JP) .............................. JP2019-049943

(51) Int. Cl.
*A61B 1/045* (2006.01)
*A61C 1/00* (2006.01)
*A61B 1/00* (2006.01)
*A61B 1/24* (2006.01)
(Continued)

(52) U.S. Cl.
CPC ........ *A61C 1/0007* (2013.01); *A61B 1/00066* (2013.01); *A61B 1/045* (2013.01); *A61B 1/24* (2013.01); *A61C 9/0053* (2013.01); *H04N 5/23245* (2013.01)

(58) Field of Classification Search
USPC ..................................................... 433/29, 26
See application file for complete search history.

(56) References Cited

U.S. PATENT DOCUMENTS

| 6,086,366 A | * | 7/2000 | Mueller | ............. B23K 26/0648 |
| | | | | 433/29 |
| 8,279,450 B2 | * | 10/2012 | Oota | ........................ A61B 1/24 |
| | | | | 433/29 |
| 9,675,428 B2 | * | 6/2017 | Wu | ....................... A61B 5/4547 |

(Continued)

FOREIGN PATENT DOCUMENTS

JP 2016-529959 A 9/2016
JP 2017-525411 A 9/2017
(Continued)

OTHER PUBLICATIONS

Office Action issued in the counterpart Japanese Patent Application No. 2019-049943, dated Jun. 1, 2021 (10 pages).
(Continued)

*Primary Examiner* — Clayton E. LaBalle
*Assistant Examiner* — Warren K Fenwick
(74) *Attorney, Agent, or Firm* — Osha Bergman Watanabe & Burton LLP

(57) ABSTRACT

A handheld dental instrument includes a casing provided with a holding portion to be held by a user, a reception unit provided on the casing to receive an operation from the user, and a control unit that controls a control target to perform a predetermined action in response to the operation received by the reception unit. The control unit performs a first control when the operation received by the reception unit from the user is a first operation, and performs a second control different from the first control when the operation received by the reception unit from the user is a second operation different from the first operation.

14 Claims, 9 Drawing Sheets

(51) Int. Cl.
    *A61C 9/00*           (2006.01)
    *H04N 5/232*        (2006.01)

(56)                  References Cited

U.S. PATENT DOCUMENTS

| | | |
|---|---|---|
| 2010/0092914 A1 | 4/2010 | Mora |
| 2014/0248576 A1* | 9/2014 | Tchouprakov ......... A61B 1/253 |
| | | 433/29 |
| 2015/0017598 A1 | 1/2015 | Wu et al. |
| 2016/0000537 A1 | 1/2016 | Schneider |
| 2016/0259515 A1 | 9/2016 | Sabina et al. |
| 2017/0289523 A1 | 10/2017 | Lee et al. |
| 2017/0295320 A1 | 10/2017 | Lee |

FOREIGN PATENT DOCUMENTS

| | | |
|---|---|---|
| JP | 2017-192720 A | 10/2017 |
| WO | 2015/196388 A1 | 12/2015 |

OTHER PUBLICATIONS

Extended European Search Report issued in European Application No. 20163538.0, dated Jul. 9, 2020 (8 pages).
Office Action issued in the counterpart Japanese Patent Application No. 2019-049943, dated Aug. 31, 2021 (5 pages).

* cited by examiner

| SINGLE-CLICK | SWITCH BETWEEN STANDBY MODE AND SCAN MODE |
| --- | --- |
| DOUBLE-CLICK | CHANGE TYPE OF DENTITION |

|  | STANDBY MODE | SCAN MODE |
|---|---|---|
| SINGLE-CLICK | SWITCH TO SCAN MODE | SWITCH TO STANDBY MODE |
| DOUBLE-CLICK | CHANGE TYPE OF DENTITION | CHANGE RESOLUTION |

FIG.7

|  | STANDBY MODE | SCAN MODE |
|---|---|---|
| SINGLE-CLICK | SWITCH TO SCAN MODE | SWITCH TO STANDBY MODE |
| DOUBLE-CLICK | SWITCH TO COLOR MODE/ MONOCHROME MODE | CHANGE RESOLUTION |
| LONG-PRESS | CHANGE TYPE OF DENTITION | SWITCH TO SNAPSHOT MODE |

INSTRUMENT IN UPRIGHT STATE

|  | STANDBY MODE | SCAN MODE |
|---|---|---|
| SINGLE-CLICK | SWITCH TO SCAN MODE | SWITCH TO STANDBY MODE |
| LONG-PRESS | CHANGE TYPE OF DENTITION | CHANGE RESOLUTION |

INSTRUMENT IN TILTED STATE

|  | STANDBY MODE | SCAN MODE |
|---|---|---|
| SINGLE-CLICK | SWITCH TO SCAN MODE | SWITCH TO STANDBY MODE |
| LONG-PRESS | SWITCH TO COLOR MODE/ MONOCHROME MODE | SWITCH TO SNAPSHOT MODE |

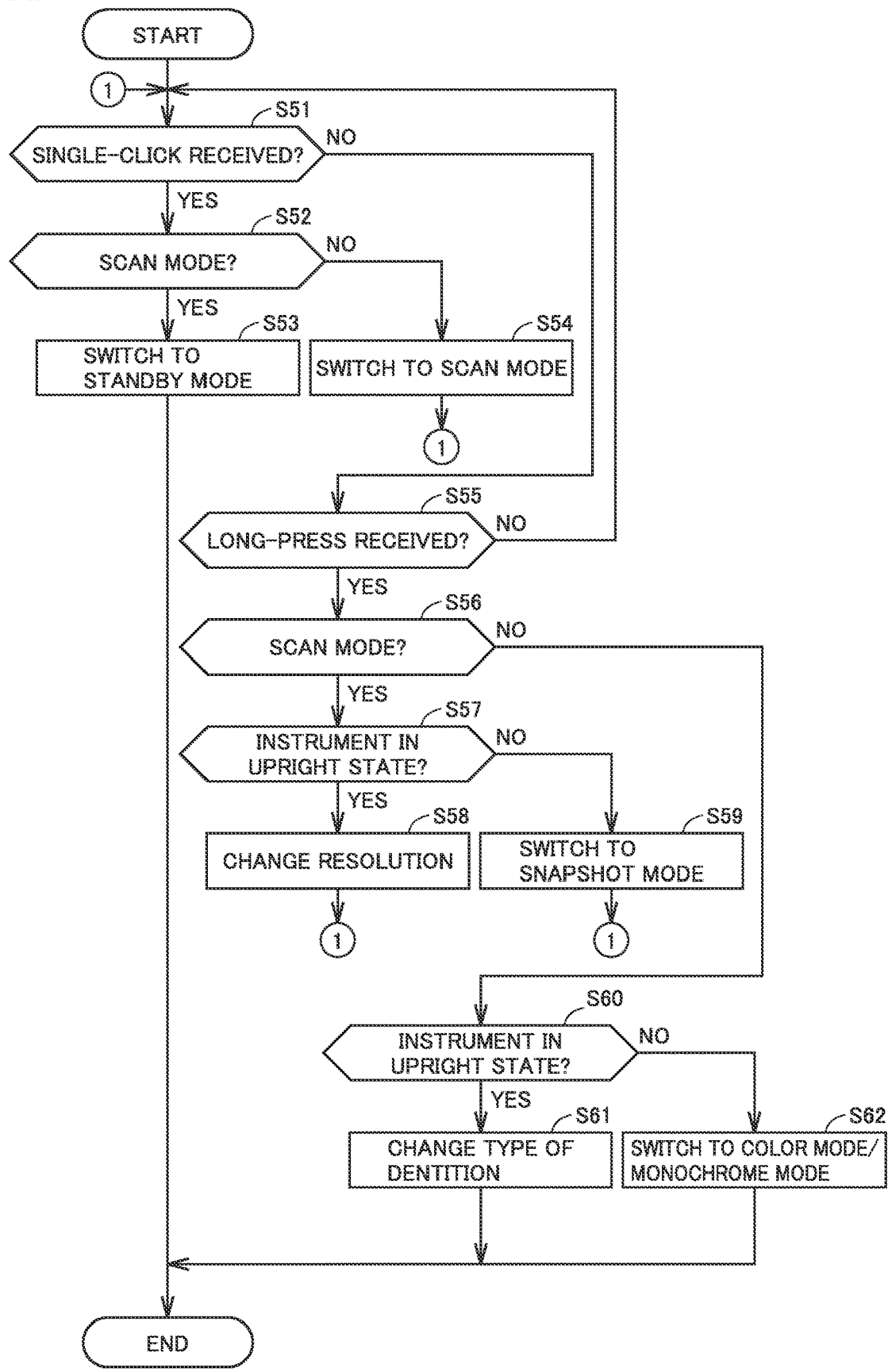

DENTAL INSTRUMENT, CONTROL METHOD THEREOF, AND THREE-DIMENSIONAL MEASURING

BACKGROUND OF THE INVENTION

Field of the Invention

The present invention relates to a handheld dental instrument, a control method thereof, and a three-dimensional measuring device.

Description of the Background Art

In the dental field, a dentist uses a dental instrument (such as a three-dimensional intraoral scanner, a 2D handy camera, a root canal treatment tool or an LED photo-polymerization device) connected to a display via a cable to examine or treat a tooth or teeth of a patient. The display shows imaged teeth, setting information of the dental instrument, activation state of the dental instrument, patient information, an instruction manual, a help screen or the like. The dentist, for example, clicks with a mouse or touches the display to change the settings so as to examine or treat a tooth or teeth of the patient.

During the examination or treatment, it is not preferable for the dentist to touch any peripheral device such as a mouse or a display in terms of sanitation. This is because the hand or fingers of the dentist may be contaminated with bacteria, viruses or the like by touching the patient's mouth during the examination or treatment.

Thus, Japanese Patent Laying-Open No. 2016-529959 discloses a technique which allows to switch an intraoral camera between manual imaging mode and automatic imaging mode by using a switch disposed thereon.

SUMMARY OF THE INVENTION

In the technique described in Japanese Patent Laying-Open No. 2016-529959, when a user (dentist) wants to perform an operation other than the switching between manual imaging mode and automatic imaging mode during the treatment, the dentist must release his/her hand from the dental instrument so as to touch the peripheral device such as the mouse or the display, which is insufficient in terms of preventing contamination.

The present invention has been made in view of the above problems, and an object thereof is to provide a dental instrument which allows a dentist to perform necessary controls without releasing his/her hand from the dental instrument during treatment, a control method thereof, and a three-dimensional measuring device.

The dental instrument according to an aspect of the present invention is a handheld dental instrument. The dental instrument includes a casing, a reception unit, and a control unit. The casing is provided with a holding portion to be held by a user. The reception unit is provided on the casing to receive an operation from the user. The control unit controls a control target to perform a predetermined action in response to the operation received by the reception unit. The control unit performs a first control when the operation received by the reception unit from the user is a first operation, and performs a second control different from the first control when the operation received by the reception unit from the user is a second operation different from the first operation.

The control method according to another aspect of the present invention is a method of controlling a handheld dental instrument in response to an operation from a user. The dental instrument includes a casing, a reception unit, and a control unit. The casing is provided with a holding portion to be held by a user. The reception unit is provided on the casing to receive an operation from the user. The control unit controls a control target to perform a predetermined action in response to the operation received by the reception unit. The control method includes performing a first control when the operation received by the reception unit from the user is a first operation, and performing a second control different from the first control when the operation received by the reception unit from the user is a second operation different from the first operation.

A three-dimensional measuring device according to still another aspect of the present invention is a handheld three-dimensional measuring device that performs a three-dimensional measurement on an object in the oral cavity. The three-dimensional measuring device includes a casing, a reception unit, and a control unit. The casing is provided with a holding portion to be held by a user. The reception unit is provided on the casing to receive an operation from the user. The control unit performs a three-dimensional measurement in response to an operation received by the reception unit. When the three-dimensional measurement is not performed, the control unit performs the three-dimensional measurement if the operation received by the reception unit from the user is a simple operation. When the three-dimensional measurement is being performed, the control unit stops the three-dimensional measurement if the operation received by the reception unit from the user is the simple operation. If the operation received by the reception unit from the user is a complicated operation that is more complicated than the simple operation, the control unit at least changes the amount of data to be obtained by the three-dimensional measurement, changes the quality of an image to be generated based on data to be obtained by the three-dimensional measurement, changes a method of performing the three-dimensional measurement, and/or generates an image of the object during the three-dimensional measurement.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a diagram illustrating a control table for the control unit according to a third embodiment;

FIG. 14 is a flowchart illustrating a process performed by the control unit according to the fifth embodiment.

DESCRIPTION OF THE PREFERRED EMBODIMENTS

Figure 1:
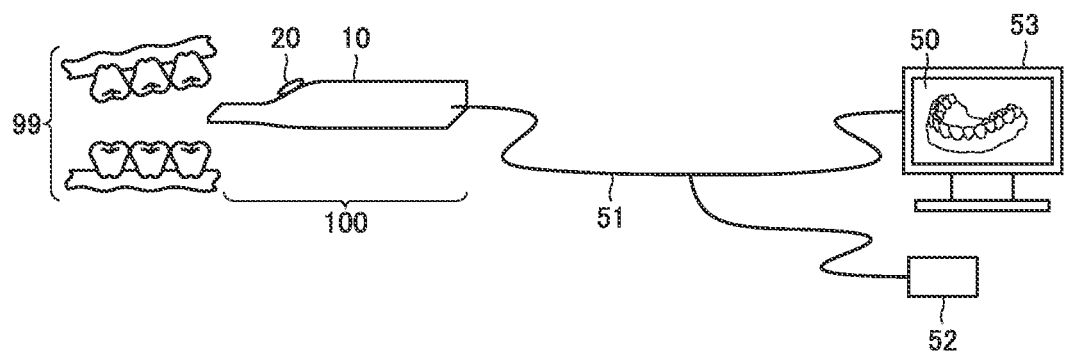
FIG. 1 is a diagram illustrating a three-dimensional scanner and peripheral devices according to a first embodiment.

Hereinafter, each embodiment will be described in detail with reference to the drawings. In the drawings, the same or corresponding portions are denoted by the same reference numerals, and the description thereof will not be repeated.

First Embodiment

A dental instrument according to a first embodiment is a three-dimensional scanner (intraoral scanner) that is used to acquire a three-dimensional shape of an intraoral dentition. However, the dental instrument according to the present invention is not limited to a three-dimensional intraoral scanner, and it may be an imaging device such as an intraoral 2D handy camera or the like. In addition, the dental instrument according to the present invention may be a root canal treatment device or a non-imaging device such as an LED photo-polymerization device. In other words, the dental instrument according to the present invention may be any dental instrument that is inserted into the oral cavity and used for dental treatment, prevention and medical examination.

FIG. 1 is a diagram illustrating a three-dimensional scanner 100 and peripheral devices according to the first embodiment. The three-dimensional scanner 100 is connected to peripheral devices such as an image processing device 53 including a display unit 50 and a power supply unit 52 via a cable 51.

The three-dimensional scanner 100 includes a casing 10. The casing 10 has a columnar shape. A user (dentist) holds a part of the casing 10 from the top or bottom side (in the vertical direction of the paper face), and inserts a tip portion of the three-dimensional scanner 100 into the oral cavity so as to measure the shape of an object 99. The object 99 refers to teeth in the oral cavity. The casing 10 is provided with a reception unit 20 that receives an operation from the user (hereinafter will be referred to as "user's operation" as necessary). The user's operation includes a single operation (for example, a single-click operation, a touch operation, or a single-scale dial operation) performed in a predetermined period, and a multiple operation performed in a predetermined period. The multiple operation includes a case where the single operation is repeatedly performed for a plurality of times in the predetermined period (for example, a double-click operation, a swipe operation, or a multi-scale dial operation) or a case where the single operation is continued in the predetermined period (for example, a long-press operation or a hold operation). The single operation is a simple operation in which the user's operation is simpler than the multiple operation, and the multiple operation is a complicated operation in which the user's operation is more complicated than the single operation.

In FIG. 1, the reception unit 20 is illustrated as a single button protruding from the casing 10, but it may be a single capacitive touch panel or a single dial. When the reception unit 20 is a button, the reception unit 20 receives a single-click operation, a double-click operation, or a long-press operation. When the reception unit 20 is a capacitive touch panel, the reception unit 20 receives a touch operation, a swipe operation, or a hold operation. When the reception unit 20 is a dial, the reception unit 20 receives a single-scale dial operation or a multi-scale dial operation. The reception unit 20 may be a combination of a button and a capacitive touch panel or a combination of a button and a dial.

The display unit 50 is a display device for displaying the obtained three-dimensional shape of the object 99. Further, the display unit 50 may be used as a display device for displaying other information such as setting information of an imaging unit 30 (see FIG. 2) to be described later, patient information, activation state of the scanner, an instruction manual, a help screen or the like. The display unit 50 may be a stationary liquid crystal display, a head-mounted wearable display, or an eye-glass type wearable display, or the like. In addition, the display unit 50 may be provided to include a plurality of screens, and thereby, the obtained three-dimensional shape and other information may be displayed as a whole on the display unit 50 or may be displayed as divisions on the plurality of screens. The image processing device 53 combines the three-dimensional measurement data acquired by the three-dimensional scanner 100 to generate an image of a dental arch.

The power supply unit 52 is a device for supplying electrical power to drive the three-dimensional scanner 100 and the display unit 50. The power supply unit 52 may be provided outside the three-dimensional scanner 100 as illustrated in FIG. 1 or may be provided inside the three-dimensional scanner 100. Further, a plurality of power supply units 52 may be provided so as to supply the electrical power to the three-dimensional scanner 100 and the display unit 50 individually.

Figure 2:
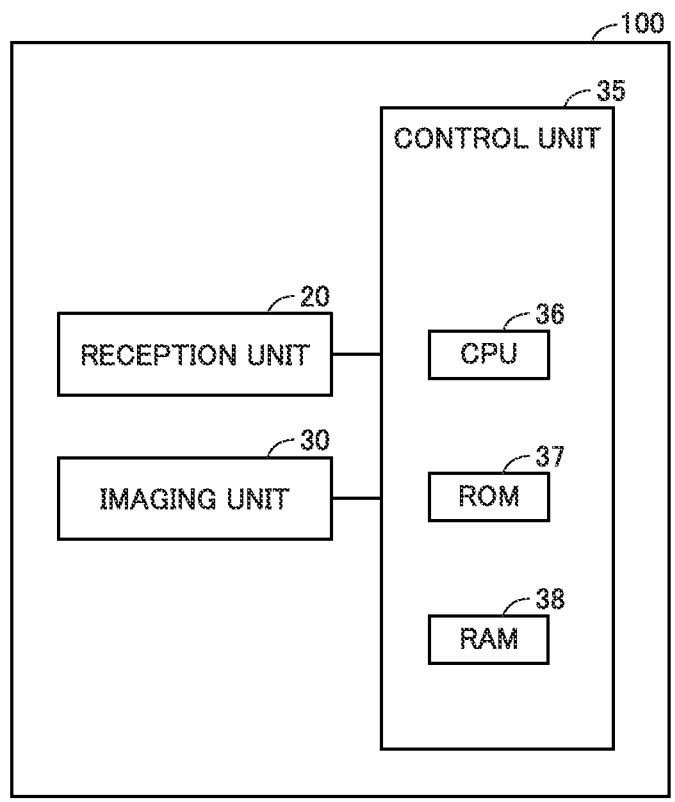
FIG. 2 is a block diagram illustrating components of the three-dimensional scanner according to the first embodiment.

FIG. 2 is a block diagram illustrating components of the three-dimensional scanner 100 according to the first embodiment. The three-dimensional scanner 100 includes a reception unit 20, an imaging unit 30, and a control unit 35.

The reception unit 20 has been described with reference to FIG. 1. The imaging unit 30 projects a pattern on the object 99 and captures an image of the projected pattern. The imaging unit 30 includes a component that changes the position of the projection pattern and the focal point of an optical sensor, and acquires a three-dimensional shape by optical manner. The control unit 35 controls the imaging unit 30 in response to an operation received by the reception unit 20. The control unit 35 includes a CPU (Central Processing Unit) 36, a ROM (Read Only Memory) 37, a RAM (Random Access Memory) 38, and the like. The CPU 36 retrieves various processing programs stored in the ROM 37, deploys the retrieved programs in the RAM 38, and controls the imaging unit 30 according to the deployed programs.

Figures 3, 4:
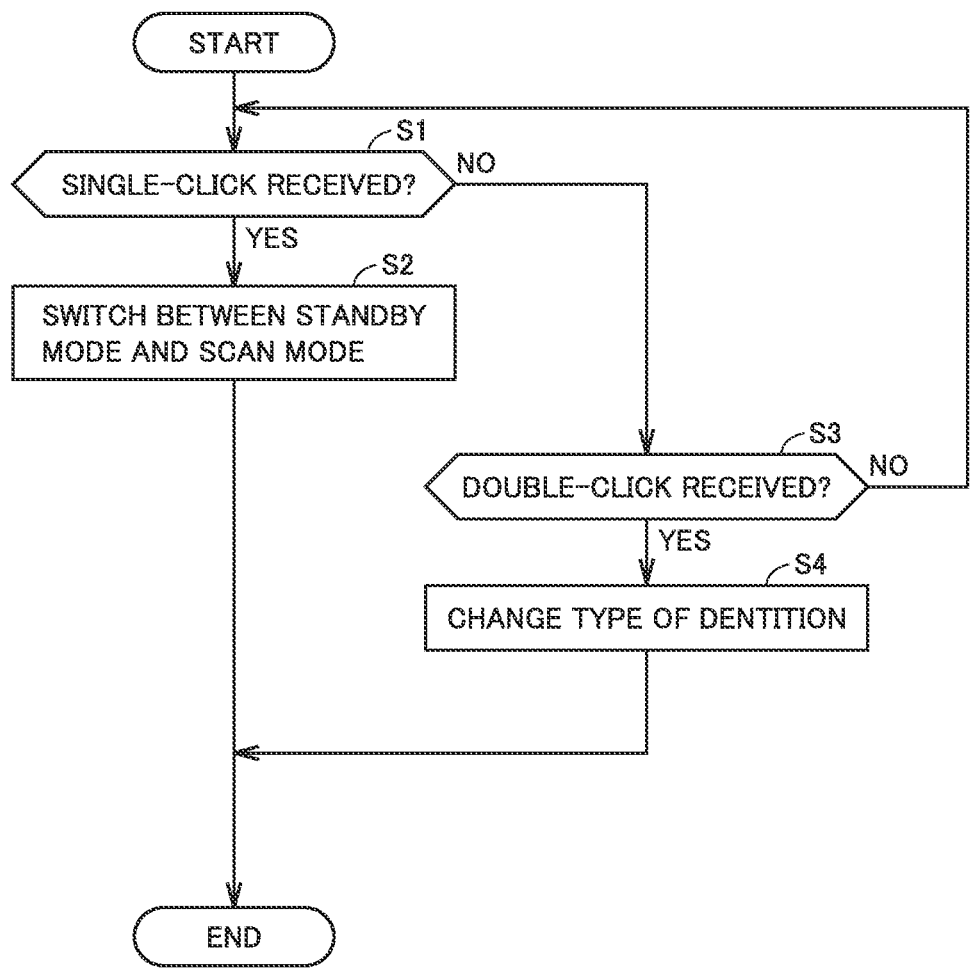
FIG. 3 is a diagram illustrating a control table for a control unit according to the first embodiment.
FIG. 4 is a flowchart illustrating a process performed by the control unit according to the first embodiment.

The control unit 35 controls the imaging unit 30 in response to the operations received by the reception unit 20 from the user. The operations received by the reception unit 20 from the user include two types: a single-click operation and a double-click operation. Hereinafter, the controls performed by the control unit 35 in response to each operation from the user will be described with reference to FIG. 3. FIG. 3 is a diagram illustrating a control table for the control unit 35 according to the first embodiment.

As illustrated in FIG. 3, when the reception unit 20 receives a single-click operation from the user, the control unit 35 switches between a standby mode and a scan mode. Thus, when the user single-clicks the reception unit 20 during the standby mode, a scan operation is started, and when the user single-clicks the reception unit 20 during the scan mode, the scan operation is stopped.

When the reception unit 20 receives a double-click operation from the user, the control unit 35 changes the type of a dentition image (hereinafter referred to as "type of dentition"). There are three types of dentition: an upper dental arch, a lower dental arch, and an engaging (biting) state. When imaging a tooth in the oral cavity, the user is required to specify the type of dentition to which the tooth belongs.

Hereinafter, the reason why it is required to specify the type of dentition will be described. The three-dimensional scanner 100 transmits the three-dimensional measurement data acquired continuously from the scanning performed by the user on the object 99 to the image processing device 53 as required. The image processing device 53 performs an image synthesis process of synthesizing a plurality of images in an image generation application based on three-dimensional position information that is included in a plurality of three-dimensional measurement data received from the three-dimensional scanner 100. In the image synthesis process, an image is synthesized for each type of dentition based on the three-dimensional measurement data stored in a predetermined folder for each type of dentition, and thereby, the user is required to specify the type of dentition. Conventionally, the user is required to click with a mouse or touch the type of dentition displayed on the display unit 50 so as to specify the type of dentition. In contrast, in the first embodiment, the control unit 35 switches the type of dentition in the order of the lower dental arch, the upper dental arch and the engaging (biting) state each time when the reception unit 20 receives a double-click operation. Thus, the user may switch between the standby mode and the scan mode by single-clicking the single reception unit 20 and change the type of dentition by double-clicking the single reception unit 20.

FIG. 4 is a flowchart illustrating a process performed by the control unit 35 according to the first embodiment. The process is performed by the control unit 35 to achieve the controls illustrated in FIG. 3, and is implemented by the CPU 36 by executing a predetermined program stored in the ROM 37.

First, the control unit 35 determines whether or not a single-click operation is received by the reception unit 20 (step S1). If a single-click operation is received by the reception unit 20 (YES in step S1), the control unit 35 switches between the standby mode and the scan mode (step S2), and ends the process illustrated in FIG. 4. On the contrary, if a single-click operation is not received by the reception unit 20 (NO in step S1), the control unit 35 proceeds the process to step S3.

In step S3, the control unit 35 determines whether or not a double-click operation is received by the reception unit 20. If a double-click operation is received by the reception unit 20 (YES in step S3), the control unit 35 changes the type of dentition (step S4), and ends the process illustrated in FIG. 4. On the contrary, if a double-click operation is not received by the reception unit 20 (NO in step S3), the control unit 35 returns the process to step S1.

As described above, the three-dimensional scanner 100 according to the first embodiment includes a casing 10 provided with a holding portion to be held by the user, a reception unit 20 provided on the casing 10 to receive an operation from the user, and a control unit 35 that controls the imaging unit 30 to perform a predetermined action in response to the operation received by the reception unit 20. When a single-click operation is received by the reception unit 20, the control unit 35 switches between the standby mode and the scan mode; and when a double-click operation is received by the reception unit 20, the control unit 35 changes the type of dentition which is conventionally achieved by operating a peripheral device such as a mouse or the display unit 50.

Accordingly, in the first embodiment, the user can change the type of dentition by double-clicking the reception unit 20 that is used for switching between the standby mode and the scan mode. In other words, the user can perform the operations such as changing the type of dentition without releasing his/her hand from the dental instrument, which prevents the contamination of bacteria, and thereby achieves sanitation.

In addition, in the first embodiment, the user does not need to touch peripheral devices such as a mouse and the display unit 50 when changing the type of dentition, and therefore there is no need to prepare a disposable glove or cover for operating the peripheral devices, which contributes to low cost and resource saving. In addition, since it is not necessary to wear a disposable glove or cover at the time of changing the type of dentition, it is possible to improve usability and work efficiency for the user.

Further, in the first embodiment, the user can change the type of dentition by performing, on the reception unit 20 that is used for switching between the standby mode and the scan mode, an operation (for example, a double-click operation) that is different from the operation for switching between the standby mode and the scan mode (for example, a single-click operation). In other words, a small number of the reception unit 20 may be used to perform the other controls in addition to the switching of the standby mode and the scan mode, which makes it possible to reduce cost and improve usability.

Furthermore, in the first embodiment, the switching of the type of dentition, which is inevitably performed when imaging the teeth in the oral cavity, can be quickly done at the user's hand, which contributes to a reduction in imaging time so as to improve the user's work efficiency and reduce the burden on the patient.

In the first embodiment, the controls performed in response to the user's operation on the reception unit 20 are described as switching between the scan mode and the standby mode and changing the type of dentition, but are not limited thereto. The controls performed in response to the user's operation on the reception unit 20 may include changing the resolution, switching between a color mode and a monochrome mode, switching to a snapshot mode, confirming the three-dimensional shape, rewinding scanned images, deleting a scanned image, replacing upper jaw image data with lower jaw image data or vice versa, or selecting an anchor tooth. Changing the resolution means increasing the density of image data in the X and Y coordinates when the image is a two-dimensional image, and further increasing the density of image data in the Z coordinate when the image is a three-dimensional image.

The control unit 35 may be configured to switch between the scan mode and the standby mode when the user's operation performed on the reception unit 20 is a simple operation, and when the user's operation performed on the reception unit 20 is a complicated operation, the control unit 35 may be configured to at least change the amount of data to be obtained by the three-dimensional measurement (for example, change the resolution, switch between a color mode and a monochrome mode), change the quality of an image to be generated based on data to be obtained by the three-dimensional measurement (for example, switch between low image quality and high image quality), change a method of performing the three-dimensional measurement (for example, change the type of dentition), and/or generate an image of the object 99 during the three-dimensional measurement (for example, take a snapshot).

In addition, the controls performed in response to the user's operation on the reception unit 20 may be arbitrarily selected and set by the user.

Hereinafter, an example scan operation by the three-dimensional scanner 100 according to the first embodiment will be described. In the present embodiment, it is assumed that the user scans the teeth in the order of the lower dental arch, the upper dental arch, and the engaging (biting) state.

First step: When the user initializes a scanning software, the lower dental arch is selected as the type of dentition to be scanned.

Second step: The user turns on the power of the three-dimensional scanner 100, wears gloves, and attaches an autoclaved (sterilized) tip to the three-dimensional scanner 100.

Third step: The user picks up the three-dimensional scanner 100, and inserts it into the patient's mouth. The user points the tip toward the lower dental arch to be scanned.

Fourth step: The user single-clicks the reception unit 20 to start the scanning of the lower dental arch (step S2).

Fifth step: The user moves the three-dimensional scanner 100 along the dentition to scan the teeth. The user scans all necessary areas while watching a multi-view displayed on the display unit 50.

Sixth step: After the scanning of the lower dental arch is completed, the user single-clicks the reception unit 20 to stop the scanning (step S2).

Seventh step: The user double-clicks the reception unit 20 to switch the type of dentition to the upper dental arch (step S4). Note that after the scanning of the lower dental arch is completed in the sixth step, the type of dentition may be switched to the upper dental arch by double-clicking the reception unit 20 without stopping the scanning.

Eighth step: The user single-clicks the reception unit 20 to start the scanning of the upper dental arch (step S2).

Ninth step: The user moves the three-dimensional scanner 100 along the dentition to scan the teeth. The user scans all necessary areas while watching a multi-view displayed on the display unit 50.

Tenth step: After the scanning of the upper dental arch is completed, the user single-clicks the reception unit 20 to stop the scanning (step S2).

Eleventh step: The user double-clicks the reception unit 20 to switch the type of dentition to the engaging (biting) state (step S4). Note that after the scanning of the upper dental arch is completed in the tenth step, the type of dentition may be switched to the engaging (biting) state by double-clicking the reception unit 20 without stopping the scanning.

Twelfth step: The user single-clicks the reception unit 20 to start the scanning of the engaging (biting) state (step S2).

Thirteenth step: The user moves the three-dimensional scanner 100 along the dentition to scan the teeth. The user scans all necessary areas while watching a multi-view displayed on the display unit 50.

Fourteenth step: After the scanning of the engaging (biting) state is completed, the user single-clicks the reception unit 20 to stop the scanning (step S2).

Fifteenth step: After the data obtained by scanning the lower dental arch, the data obtained by scanning the upper dental arch, and the data obtained by scanning the engaging (biting) state are synthesized on the scanning software, the user places the three-dimensional scanner 100 back to the cradle.

Sixteenth step: The user turns off the power of the three-dimensional scanner 100 by pressing the power button for three seconds or more.

After the above steps, the user converts the three-dimensional shape of the teeth obtained by the scanning into STL (Standard Triangulated Language) data. The converted STL data may be used in creating an implant, managing three-dimensional dental arch data as an electronic medical record, or diagnosing a disease such as dental caries.

Second Embodiment

In the first embodiment, the control unit 35 performs different controls in response to the operations received by the reception unit 20 regardless of whether or not the current mode is the scan mode. In contrast, in the second embodiment, the control unit performs different controls depending on whether or not the current mode is the scan mode and the operations received by the reception unit. Since the configuration of the three-dimensional scanner according to the second embodiment is the same as the configuration of the three-dimensional scanner 100 according to the first embodiment, the same components are denoted by the same reference numerals, and the description thereof will not be repeated.

Figures 5, 6:
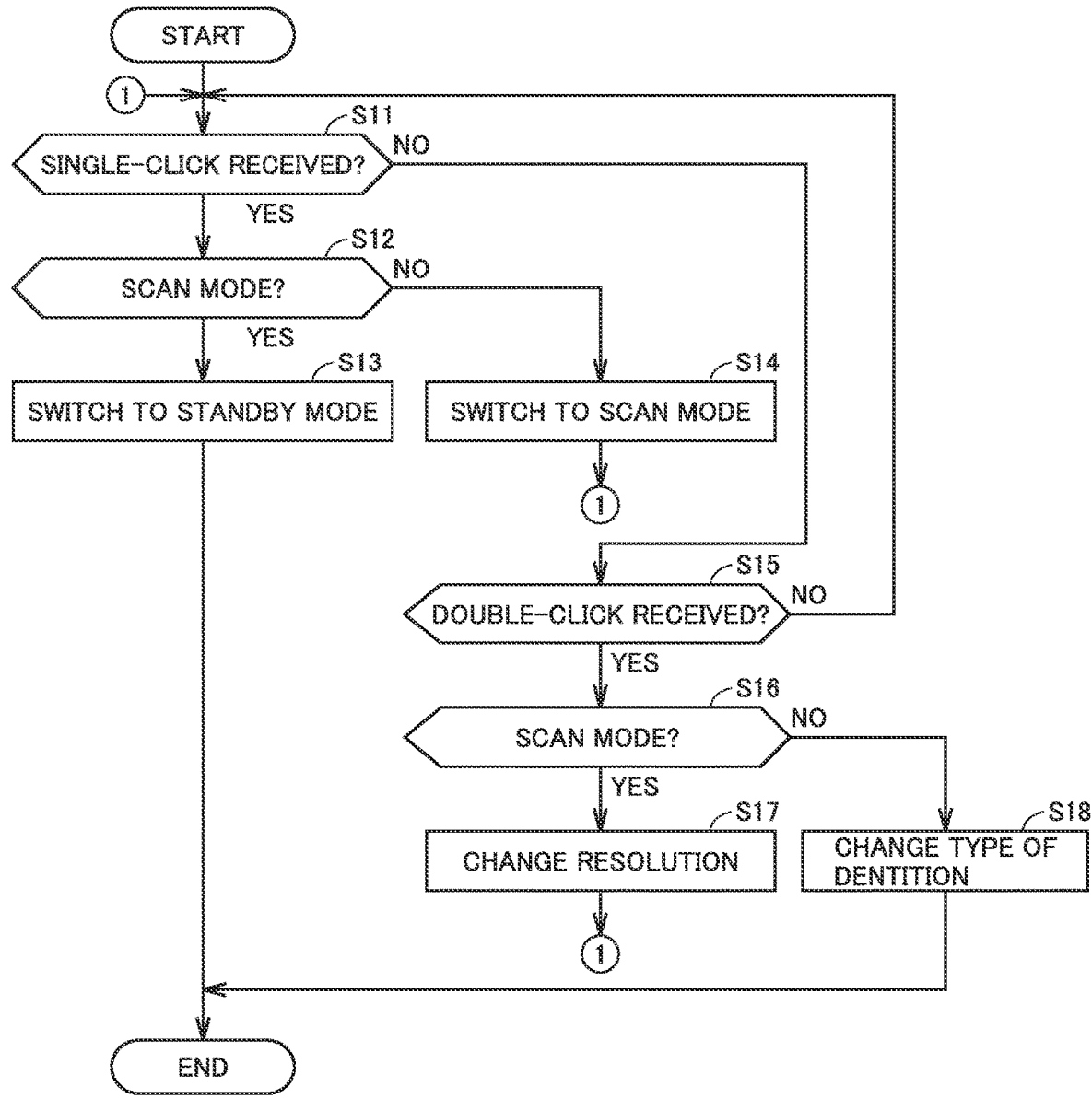
FIG. 5 is a diagram illustrating a control table for the control unit according to a second embodiment.
FIG. 6 is a flowchart illustrating a process performed by the control unit according to the second embodiment.

FIG. 5 is a diagram illustrating a control table for the control unit 35 according to the second embodiment. The three-dimensional scanner 100 has a standby mode and a scan mode. The standby mode is a mode in which a tooth in the oral cavity is not allowed to be imaged, and may be switched to the scan mode. In contrast, the scan mode is a mode in which a tooth in the oral cavity is allowed to be imaged. In the scan mode, the imaging unit 30 continuously captures images of a plurality of teeth and generates a dentition image based on the images.

When the reception unit 20 receives a single-click operation from the user during the standby mode, the control unit 35 switches the standby mode to the scan mode. On the contrary, when the reception unit 20 receives a single-click operation from the user during the scan mode, the control unit 35 switches the scan mode to the standby mode. Thus, the user may switch between the standby mode and the scan mode simply by performing a single-click operation on the reception unit 20.

When the reception unit 20 receives a double-click operation from the user during the standby mode, the control unit 35 changes the type of dentition. Specifically, the control unit 35 changes the type of dentition in the order of the lower dental arch, the upper dental arch, and the engaging (biting) state each time when the reception unit 20 receives a double-click operation during the standby mode. Thus, the user may change the type of dentition simply by performing a double-click operation on the reception unit 20 during the standby mode.

When the reception unit 20 receives a double-click operation from the user during the scan mode, the control unit 35 changes the resolution in the imaging mode. The resolution includes a standard resolution and a high resolution, and the user images the teeth in the oral cavity while changing the resolution as necessary. Conventionally, the user changes the resolution by clicking with a mouse or touching the standard resolution and the high resolution displayed on the display unit 50. In contrast, in the second embodiment, the control unit 35 changes the resolution when the reception unit 20 receives a double-click operation during the scan mode. Thus, the user may change the resolution simply by performing a double-click operation on the reception unit 20 during the scan mode. Note that the resolution is not limited to two types, i.e., the standard resolution and the high resolution, and may be three types or more. Changing the resolution means increasing the density of image data in the X and Y coordinates when the image is a two-dimensional image, and further increasing the density of image data in the Z coordinate when the image is a three-dimensional image.

FIG. 6 is a flowchart illustrating a process performed by the control unit 35 according to the second embodiment. The process is performed by the control unit 35 so as to achieve the controls illustrated in FIG. 5, and is realized by the CPU 36 executing a predetermined program stored in the ROM 37.

First, the control unit 35 determines whether or not a single-click operation is received by the reception unit 20 (step S11). If a single-click operation is received by the reception unit 20 (YES in step S11), the control unit 35 proceeds the process to step S12. On the contrary, if a single-click operation is not received by the reception unit 20 (NO in step S11), the control unit 35 proceeds the process to step S15.

In step S12, the control unit 35 determines whether or not the current mode is the scan mode. If the current mode is the scan mode (YES in step S12), the control unit 35 switches the scan mode to the standby mode (step S13), and ends the process illustrated in FIG. 6. On the contrary, if the current mode is not the scan mode, in other words, if the current mode is the standby mode (NO in step S12), the control unit 35 switches the standby mode to the scan mode (step S14), and returns the process to step S11.

In step S15, the control unit 35 determines whether or not a double-click operation is received by the reception unit 20. If a double-click operation is received by the reception unit 20 (YES in step S15), the control unit 35 proceeds the process to step S16. On the contrary, if a double-click operation is not received by the reception unit 20 (NO in step S15), the control unit 35 returns the process to step S11.

In step S16, the control unit 35 determines whether or not the current mode is the scan mode. If the current mode is the scan mode (YES in step S16), the control unit 35 changes the resolution (step S17), and returns the process to step S11. On the contrary, if the current mode is not the scan mode, in other words, if the current mode is the standby mode (NO in step S16), the control unit 35 changes the type of dentition (step S18), and ends the process illustrated in FIG. 6.

As described above, the three-dimensional scanner 100 according to the second embodiment includes a casing 10 provided with a holding portion to be held by the user, a reception unit 20 provided on the casing 10 to receive an operation from the user, and a control unit 35 that controls the imaging unit 30 to perform a predetermined action in response to the operation received by the reception unit 20. When a single-click operation is received by the reception unit 20, the control unit 35 switches between the scan mode and the standby mode; and when a double-click operation is received by the reception unit 20, the control unit 35 changes the type of dentition or changes the imaging mode or the like which is conventionally achieved by operating a peripheral device such as a mouse or the display unit 50. As an example, when a double-click operation is received during the standby mode, the control unit 35 changes the type of dentition, and when a double-click operation is received during the scan mode, the control unit 35 changes the resolution.

Accordingly, in the second embodiment, the user can change the type of dentition and the imaging mode by double-clicking the reception unit 20 that is used for switching between the scan mode and the standby mode. In other words, the user can perform the operations such as changing the type of dentition and changing the imaging mode without releasing his/her hand from the dental instrument, which prevents the contamination of bacteria, and thereby achieves sanitation.

In addition, in the second embodiment, the user does not need to touch the peripheral devices such as a mouse and the display unit 50 when changing the type of dentition or changing the imaging mode, and therefore there is no need to prepare a disposable glove or cover for operating the peripheral devices, which contributes to low cost and resource saving. In addition, since it is not necessary to wear a disposable glove or cover at the time of changing the type of dentition or changing the imaging mode, it is possible to improve usability and work efficiency for the user.

Further, in the second embodiment, based on a combination of an operation (for example, a double-click operation) performed by the user on the reception unit 20 that is used for switching between the standby mode and the scan mode and whether or not the current mode is the scan mode, a maximum number of two different controls (such as changing the type of dentition and changing the resolution) can be performed. In other words, a small number of the reception unit 20 may be used to perform various controls, which makes it possible to reduce cost and improve usability.

Furthermore, in the second embodiment, the switching of the type of dentition, which is inevitably performed when imaging the teeth in the oral cavity, can be quickly done at the user's hand, which contributes to a reduction in imaging time so as to improve the user's work efficiency and reduce the burden on the patient.

In the second embodiment, only one reception unit 20 is provided on the casing 10, it is also acceptable to provide a plurality of reception units 20. For example, the casing 10 may be provided with a reception unit that is used for switching between the scan mode and the standby mode and a reception unit that is used for changing the type of dentition or changing the imaging mode. However, in consideration of cost and usability, it is preferred that the number of reception units 20 is as small as possible.

In the second embodiment, the controls performed in response to the user's operation on the reception unit 20 are described as switching between the scan mode and the standby mode, changing the type of dentition and changing the resolution, but are not limited thereto. The controls performed in response to the user's operation on the reception unit 20 may include switching between a color mode and a monochrome mode, switching to a snapshot mode, confirming the three-dimensional shape, rewinding scanned images, deleting a scanned image, replacing upper jaw image data with lower jaw image data or vice versa, or selecting an anchor tooth. Further, the user may arbitrarily select and set the contents of a control to be performed in response to a user's operation on the reception unit 20.

Hereinafter, an example scan operation by the three-dimensional scanner 100 according to the second embodiment will be described. In the present embodiment, it is assumed that the user scans the teeth in the order of the lower dental arch, the upper dental arch, and the engaging (biting) state.

First step: When the user initializes a scanning software, the lower dental arch is selected as the type of dentition to be scanned.

Second step: The user turns on the power of the three-dimensional scanner 100, wears gloves, and attaches an autoclaved (sterilized) tip to the three-dimensional scanner 100.

Third step: The user picks up the three-dimensional scanner 100, and inserts it into the patient's mouth. The user points the tip toward the lower dental arch to be scanned.

Fourth step: The user single-clicks the reception unit 20 to start the scanning of the lower dental arch (step S14).

Fifth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S17).

Sixth step: After the scanning of the lower dental arch is completed, the user single-clicks the reception unit 20 to stop the scanning (step S13).

Seventh step: The user double-clicks the reception unit 20 to switch the type of dentition to the upper dental arch (step S18).

Eighth Step: The user single-clicks the reception unit 20 to start the scanning of the upper dental arch (step S14).

Ninth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S17).

Tenth step: After the scanning of the upper dental arch is completed, the user single-clicks the reception unit 20 to stop the scanning (step S13).

Eleventh step: The user double-clicks the reception unit 20 to switch the type of dentition to the engaging (biting) state (step S18).

Twelfth step: The user single-clicks the reception unit 20 to start the scanning of the engaging (biting) state (step S14).

Thirteenth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S17).

Fourteenth step: After the scanning of the engaging (biting) state is completed, the user single-clicks the reception unit 20 to stop the scanning (step S13).

Fifteenth step: After the data obtained by scanning the lower dental arch, the data obtained by scanning the upper dental arch, and the data obtained by scanning the engaging (biting) state are synthesized on the scanning software, the user places the three-dimensional scanner 100 back to the cradle.

Sixteenth step: The user turns off the power of the three-dimensional scanner 100 by pressing the power button for three seconds or more.

After the above steps, the user converts the three-dimensional shape of the teeth obtained by the scanning into STL (Standard Triangulated Language) data. The converted STL data may be used in creating an implant, managing three-dimensional dental arch data as an electronic medical record, or diagnosing a disease such as dental caries.

Third Embodiment

In the first embodiment, the control unit 35 performs different controls in response to the operations received by the reception unit 20 regardless of whether or not the current mode is the scan mode. Further, in the first embodiment, the user's operations that may be received by the reception unit 20 include only two types: the single-click operation and the double-click operation. In contrast, in the third embodiment, the control unit performs different controls depending on whether or not the current mode is the scan mode and the operations received by the reception unit. In the third embodiment, the user's operations that may be received by the reception unit include three types: a single-click operation, a double-click operation, and a long-press operation. Since the configuration of the three-dimensional scanner according to the third embodiment is the same as the configuration of the three-dimensional scanner 100 according to the first embodiment, the same components are denoted by the same reference numerals, and the description thereof will not be repeated.

FIG. 7 is a diagram illustrating a control table for the control unit 35 according to the third embodiment. The three-dimensional scanner 100 has a standby mode and a scan mode. The standby mode is a mode in which a tooth in the oral cavity is not allowed to be imaged. In contrast, the scan mode is a mode in which a tooth in the oral cavity is allowed to be imaged. In the scan mode, the imaging unit 30 continuously captures images of a plurality of teeth and generates a dentition image based on the images. The user's operations that may be received by the reception unit 20 include three types: a single-click operation, a double-click operation, and a long-press operation.

When the reception unit 20 receives a single-click operation from the user during the standby mode, the control unit 35 switches the standby mode to the scan mode. On the contrary, when the reception unit 20 receives a single-click operation from the user during the scan mode, the control unit 35 switches the scan mode to the standby mode. Thus, the user may switch between the scan mode and the standby mode simply by single-clicking the reception unit 20.

When the reception unit 20 receives a double-click operation from the user during the standby mode, the control unit 35 changes the color selection mode in the imaging mode. The color selection mode includes a color mode and a monochrome mode, and the user images teeth in the oral cavity while changing the mode as necessary. Conventionally, the user changes the color selection mode by clicking with a mouse or touching the color mode and the monochrome mode displayed on the display unit 50. In contrast, in the third embodiment, the control unit 35 switches between the color mode and the monochrome mode when the reception unit 20 receives a double-click operation during the standby mode. Thereby, the user may change the color selection mode simply by double-clicking the reception unit 20 during the standby mode.

When the reception unit 20 receives a double-click operation from the user during the scan mode, the control unit 35 changes the resolution in the imaging mode. Thus, the user may change the resolution simply by double-clicking the reception unit 20 during the scan mode. Changing the resolution means increasing the density of image data in the X and Y coordinates when the image is a two-dimensional image, and further increasing the density of image data in the Z coordinate when the image is a three-dimensional image.

When the reception unit 20 receives a long-press operation from the user during the standby mode, the control unit 35 changes the type of dentition. Specifically, the control unit 35 changes the type of dentition in the order of the lower dental arch, the upper dental arch, and the engaging (biting) state each time when the reception unit 20 receives a long-press operation during the standby mode. Thus, the user may change the type of dentition simply by long-pressing the reception unit 20 during the standby mode.

If the reception unit 20 receives a long-press operation from the user during the scan mode, the control unit 35 changes the imaging mode to the snapshot mode. The user may need to take a snapshot of the teeth in the oral cavity during the scanning. Conventionally, the user changes the imaging mode to the snapshot mode by clicking with a mouse or touching a snapshot icon displayed on the display unit 50. In contrast, in the third embodiment, when the reception unit 20 receives a long-press operation during the scan mode, the control unit 35 switches the scan mode to the snapshot mode to take images. Thus, the user may switch the scan mode to the snapshot mode so as to take a snapshot simply by long-pressing the reception unit 20 during the scan mode.

Figure 8:
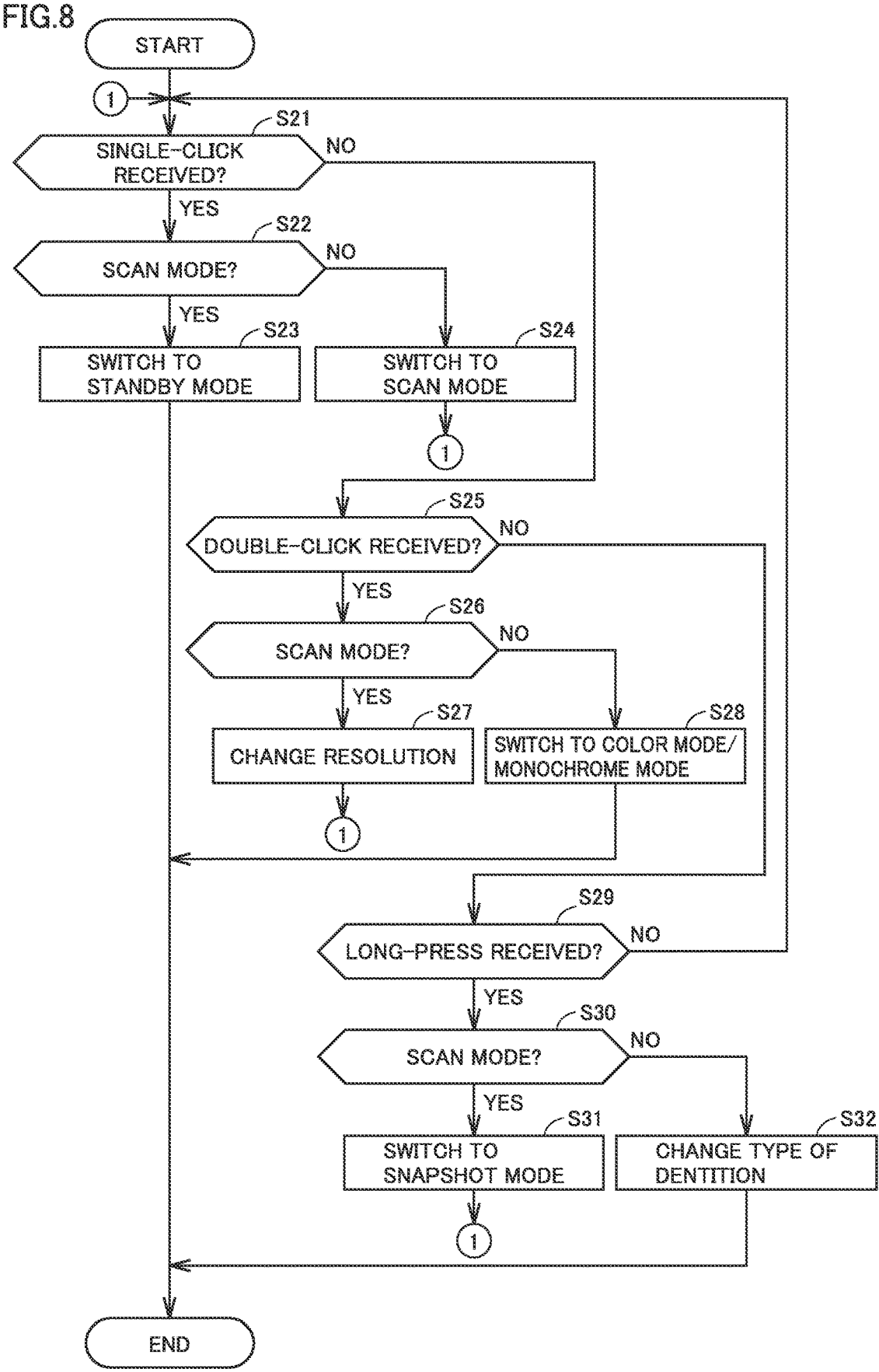
FIG. 8 is a flowchart illustrating a process performed by the control unit according to the third embodiment.

FIG. 8 is a flowchart illustrating a process performed by the control unit 35 according to the third embodiment. The process is performed by the control unit 35 so as to achieve the controls illustrated in FIG. 7, and is realized by the CPU 36 executing a predetermined program stored in the ROM 37.

First, the control unit 35 determines whether or not a single-click operation is received by the reception unit 20 (step S21). If a single-click operation is received by the reception unit 20 (YES in step S21), the control unit 35 proceeds the process to step S22. On the contrary, if a single-click operation is not received by the reception unit 20 (NO in step S21), the control unit 35 proceeds the process to step S25.

In step S22, the control unit 35 determines whether or not the current mode is the scan mode. If the current mode is the scan mode (YES in step S22), the control unit 35 switches the scan mode to the standby mode (step S23), and ends the process illustrated in FIG. 8. On the contrary, if the current mode is not the scan mode, in other words, if the current mode is the standby mode (NO in step S22), the control unit 35 switches the standby mode to the scan mode (step S24), and returns the process to step S21.

In step S25, the control unit 35 determines whether or not a double-click operation is received by the reception unit 20. If a double-click operation is received by the reception unit 20 (YES in step S25), the control unit 35 proceeds the process to step S26. On the contrary, if a double-click operation is not received by the reception unit 20 (NO in step S25), the control unit 35 proceeds the process to step S29.

In step S26, the control unit 35 determines whether or not the current mode is the scan mode. If the current mode is the scan mode (YES in step S26), the control unit 35 changes the resolution (step S27), and returns the process to step S21. On the contrary, if the current mode is not the scan mode, in other words, if the current mode is the standby mode (NO in step S26), the control unit 35 switches between the color mode and the monochrome mode (step S28), and ends the process illustrated in FIG. 8. In step S29, the control unit 35 determines whether or not a long-press operation is received by the reception unit 20. If a long-press operation is received by the reception unit 20 (YES in step S29), the control unit 35 proceeds the process to step S30. On the contrary, if a long-press operation is not received by the reception unit 20 (NO in step S29), the control unit 35 returns the process to step S21.

In step S30, the control unit 35 determines whether or not the current mode is the scan mode. If the current mode is the scan mode (YES in step S30), the control unit 35 changes the current mode to the snapshot mode (step S31), and returns the process to step S21. On the contrary, if the current mode is not the scan mode, in other words, if the current mode is the standby mode (NO in step S30), the control unit 35 changes the type of dentition (step S32), and ends the process illustrated in FIG. 8.

As described above, the three-dimensional scanner 100 according to the third embodiment includes a casing 10 provided with a holding portion to be held by the user, a reception unit 20 provided on the casing 10 to receive an operation from the user, and a control unit 35 that controls the imaging unit 30 to perform a predetermined action in response to the operation received by the reception unit 20. When a single-click operation is received by the reception unit 20, the control unit 35 switches between the scan mode and the standby mode; and when a double-click operation or a long-press operation is received by the reception unit 20, the control unit 35 changes the type of dentition or changes the imaging mode or the like which is conventionally achieved by operating a peripheral device such as a mouse or the display unit 50. As an example, when a double-click operation is received during the standby mode, the control unit 35 switches between the color mode and the monochrome mode, and when a double-click operation is received during the scan mode, the control unit 35 changes the resolution. Further, when a long-press operation is received during the standby mode, the control unit 35 changes the type of dentition, and when a long-press operation is received during the scan mode, the control unit 35 switches the scan mode to the snapshot mode.

Accordingly, in the third embodiment, the user can change the type of dentition and the imaging mode by performing an operation (for example, a double-click operation, a long-press operation or the like) on the reception unit 20 that is used for switching between the scan mode and the standby mode. In other words, the user can perform the operations such as changing the type of dentition and changing the imaging mode without releasing his/her hand from the dental instrument, which prevents the contamination of bacteria, and thereby achieves sanitation.

In addition, in the third embodiment, the user does not need to touch the peripheral devices such as a mouse and the display unit 50 when changing the type of dentition or changing the imaging mode, and therefore there is no need to prepare a disposable glove or cover for operating the peripheral devices, which contributes to low cost and resource saving. In addition, since it is not necessary to wear a disposable glove or cover at the time of changing the type of dentition or changing the imaging mode, it is possible to improve usability and work efficiency for the user.

Further, in the third embodiment, based on a combination of an operation (for example, a double-click operation or a long-press operation) performed by the user on the reception unit 20 that is used for switching between the standby mode and the scan mode and whether or not the current mode is the scan mode, a maximum number of 4 different controls (such as changing the type of dentition, changing the resolution, switching between the color mode and the monochrome mode and switching to the snapshot mode) can be performed. In other words, a small number of the reception unit 20 may be used to perform various controls, which makes it possible to reduce cost and improve usability.

Furthermore, in the third embodiment, the switching of the type of dentition, which is inevitably performed when imaging the teeth in the oral cavity, can be quickly done at the user's hand, which contributes to a reduction in imaging time so as to improve the user's work efficiency and reduce the burden on the patient.

In the third embodiment, only one reception unit 20 is provided on the casing 10, it is also acceptable to provide a plurality of reception units 20. For example, the casing 10 may be provided with a reception unit that is used for switching between the scan mode and the standby mode and a reception unit that is used for changing the type of dentition or changing the imaging mode. However, in consideration of cost and usability, it is preferred that the number of reception units 20 is as small as possible.

In the third embodiment, the controls performed in response to the user's operation on the reception unit 20 are described as switching between the scan mode and the standby mode, changing the type of dentition, changing the resolution, switching between the color mode and the monochrome mode, and switching to the snapshot mode, but are not limited thereto. The controls performed in response to the user's operation on the reception unit 20 may include confirming the three-dimensional shape, rewinding scanned images, deleting a scanned image, replacing upper jaw image data with lower jaw image data or vice versa, or selecting an anchor tooth. Further, the user may arbitrarily select and set the contents of a control to be performed in response to a user's operation on the reception unit 20.

Hereinafter, an example scan operation by the three-dimensional scanner 100 according to the third embodiment will be described. In the present embodiment, it is assumed that the user scans the teeth in the order of the lower dental arch, the upper dental arch, and the engaging (biting) state.

First step: When the user initializes a scanning software, the lower dental arch is selected as the type of dentition to be scanned.

Second step: The user turns on the power of the three-dimensional scanner 100, wears gloves, and attaches an autoclaved (sterilized) tip to the three-dimensional scanner 100.

Third step: The user picks up the three-dimensional scanner 100, and inserts it into the patient's mouth. The user points the tip toward the lower dental arch to be scanned.

Fourth step: The user single-clicks the reception unit 20 to start the scanning of the lower dental arch (step S24).

Fifth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S27). In addition, the user may switch to the snapshot mode so as to take a snapshot by long-pressing the reception unit 20 during the scanning (S31).

Sixth step: After the scanning of the lower dental arch is completed, the user single-clicks the reception unit 20 to stop the scanning (step S23).

Seventh step: The user long-presses the reception unit 20 to switch the type of dentition to the upper dental arch (step S32).

Eighth Step: The user single-clicks the reception unit 20 to start the scanning of the upper dental arch (Step S24).

Ninth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S27). In addition, the user may switch to the snapshot mode so as to take a snapshot by long-pressing the reception unit 20 during the scanning (S31).

Tenth step: After the scanning of the upper dental arch is completed, the user single-clicks the reception unit 20 to stop the scanning (step S23).

Eleventh step: The user long-presses the reception unit 20 to switch the type of dentition to the engaging (biting) state (step S32).

Twelfth step: The user single-clicks the reception unit 20 to start the scanning of the engaging (biting) state (step S24).

Thirteenth step: The user moves the three-dimensional scanner 100 along the dentition to scan the teeth. The user scans all necessary areas while watching a multi-view displayed on the display unit 50. The user may change the resolution by double-clicking the reception unit 20 during the scanning (step S27). In addition, the user may switch to the snapshot mode so as to take a snapshot by long-pressing the reception unit 20 during the scanning (S31).

Fourteenth step: After the scanning of the engaging (biting) state is completed, the user single-clicks the reception unit 20 to stop the scanning (step S23).

Fifteenth step: After the data obtained by scanning the lower dental arch, the data obtained by scanning the upper dental arch, and the data obtained by scanning the engaging (biting) state are synthesized on the scanning software, the user places the three-dimensional scanner 100 back to the cradle.

Sixteenth step: The user turns off the power of the three-dimensional scanner 100 by pressing the power button for three seconds or more.

After the above steps, the user converts the three-dimensional shape of the teeth obtained by the scanning into STL (Standard Triangulated Language) data. The converted STL data may be used in creating an implant, managing three-dimensional dental arch data as an electronic medical record, or diagnosing a disease such as dental caries.

Fourth Embodiment

In the third embodiment, the control unit 35 switches the type of dentition each time when the reception unit 20 receives a long-press operation. In contrast, in the fourth embodiment, the control unit switches the type of dentition in response to the reception of a long-press operation by the reception unit and the motion of the three-dimensional scanner.

Figure 9:
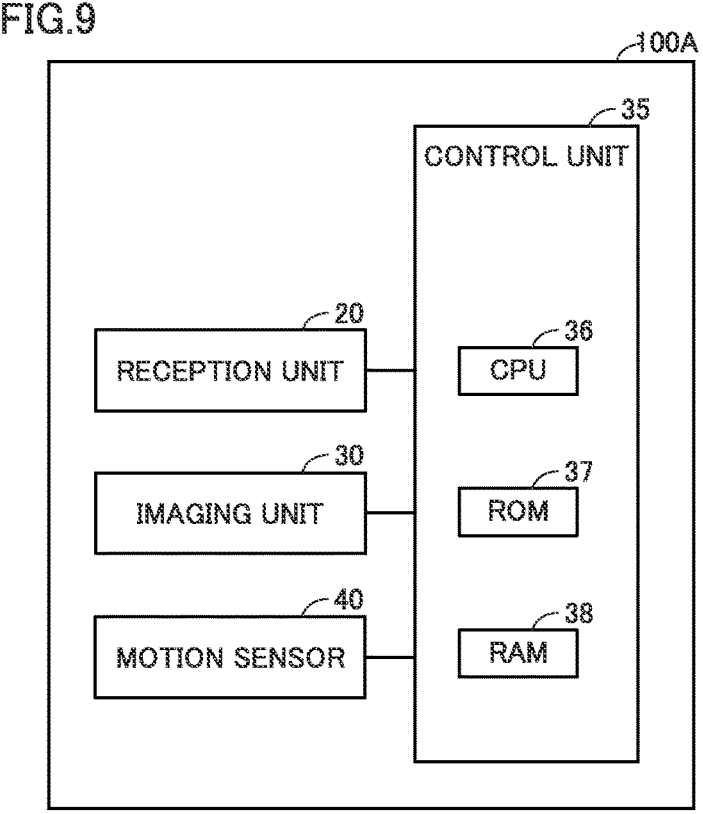
FIG. 9 is a block diagram illustrating components of a three-dimensional scanner according to a fourth embodiment.

FIG. 9 is a block diagram illustrating components of a three-dimensional scanner 100A according to the fourth embodiment. The configuration of the three-dimensional scanner 100A is different from the configuration of the three-dimensional scanner 100 in the third embodiment in that the three-dimensional scanner 100A includes a motion sensor 40 that detects the motion of the three-dimensional scanner. Since the configuration of the three-dimensional scanner 100A except the motion sensor 40 is the same as the configuration of the three-dimensional scanner 100 according to the third embodiment, the same components are denoted by the same reference numerals, and the description thereof will not be repeated. The control table for the control unit 35 according to the fourth embodiment is the same as the control table for the control unit 35 according to the third embodiment, and the description thereof will not be repeated.

Figure 10:
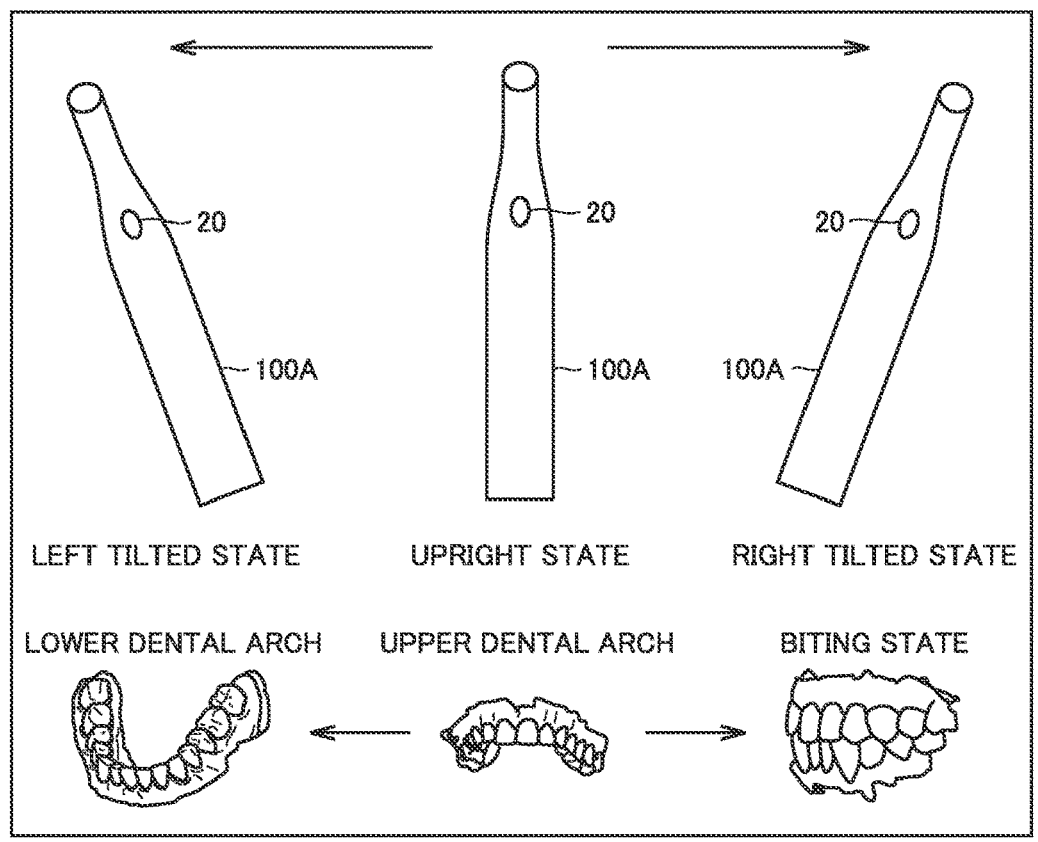
FIG. 10 is a diagram illustrating operations performed by a user so as to change the type of dentition according to the fourth embodiment.

FIG. 10 is a diagram illustrating operations performed by the user so as to change the type of dentition according to the fourth embodiment. As illustrated in FIG. 10, if the type of dentition currently selected is the upper dental arch, when the user tilts the three-dimensional scanner 100A while long-pressing the reception unit 20 during the standby mode, the type of dentition is changed. Specifically, during the standby mode, when the user tilts the three-dimensional scanner 100A from the upright state to the left while long-pressing the reception unit 20, the type of dentition is switched to the lower dental arch; and when the user tilts the three-dimensional scanner 100A from the upright state to the right while long-pressing the reception unit 20, the type of dentition is switched to the engaging (biting) state.

If the type of dentition currently selected is the lower dental arch, when the user tilts the three-dimensional scanner 100A from the upright state to the left while long-pressing the reception unit 20 during the standby mode, the type of dentition is switched to the engaging (biting) state; and when the user tilts the three-dimensional scanner 100A from the upright state to the right while long-pressing the reception unit 20, the type of dentition is switched to the upper dental arch.

If the type of dentition currently selected is the engaging (biting) state, when the user tilts the three-dimensional scanner 100A from the upright state to the left while long-pressing the reception unit 20 during the standby mode, the type of dentition is switched to the upper dental arch; and when the user tilts the three-dimensional scanner 100A from the upright state to the right while long-pressing the reception unit 20, the type of dentition is switched to the lower dental arch.

Figure 11:
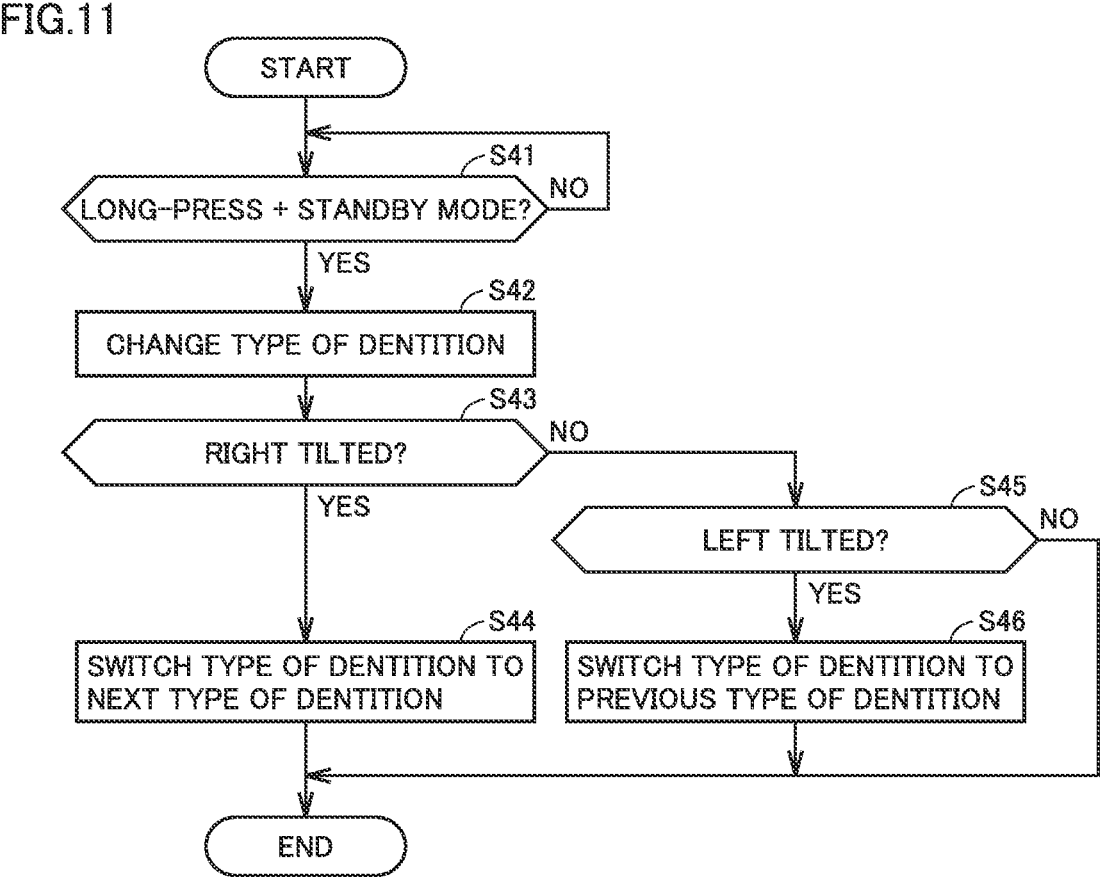
FIG. 11 is a flowchart illustrating a process performed by the control unit according to the fourth embodiment.

FIG. 11 is a flowchart illustrating a process performed by the control unit 35 according to the fourth embodiment. The process is performed by the control unit 35 so as to achieve the controls illustrated in FIG. 10, and is realized by the CPU 36 executing a predetermined program stored in the ROM 37.

First, the control unit 35 determines whether or not a long-press operation is received by the reception unit 20 during the standby mode (step S41). The control unit 35 repeats the process of step S41 until a long-press operation is received by the reception unit 20 during the standby mode, and if a long-press operation is received by the reception unit 20 during the standby mode (YES in step S41), the control unit 35 changes the type of dentition (step S42).

Next, the control unit 35 determines whether or not the three-dimensional scanner 100A is tilted from the upright state to the right (step S43). The control unit 35 determines whether or not the three-dimensional scanner 100A is tilted from the upright state to the right based on a detection result by the motion sensor 40. If the three-dimensional scanner 100A is tilted from the upright state to the right (YES in step S43), the control unit 35 switches the type of dentition to the next type of dentition (step S44), and ends the process illustrated in FIG. 11. On the contrary, if the three-dimensional scanner 100A is not tilted from the upright state to the right (NO in step S43), the control unit 35 determines whether or not the three-dimensional scanner 100A is tilted from the upright state to the left (step S45). The control unit 35 determines whether or not the three-dimensional scanner 100A is tilted from the upright state to the left based on a detection result by the motion sensor 40.

If the three-dimensional scanner 100A is tilted from the upright state to the left (YES in step S45), the control unit 35 switches the type of dentition to the previous type of dentition (step S46), and ends the process illustrated in FIG. 11. On the contrary, if the three-dimensional scanner 100A is not tilted from the upright state to the left (NO in step S45), the control unit 35 ends the process illustrated in FIG. 11 without changing the type of dentition. Note that the three-dimensional scanner 100A is not required to be placed in the upright state, and it may be placed horizontal to the floor surface. When the three-dimensional scanner 100A is placed horizontal to the floor, in order not to be confused with the case where the oral cavity is imaged, an inclination that is impossible in the oral cavity, for example, an inclination of the three-dimensional scanner 100A equal to 45° or more relative to the horizontal may be used as a determination threshold.

As described above, the three-dimensional scanner 100A according to the fourth embodiment further includes a motion sensor 40 that detects the motion of the three-dimensional scanner in addition to the configuration of the three-dimensional scanner 100 according to the third embodiment. When the three-dimensional scanner 100A is tilted while being long-pressed during the standby mode, the control unit 35 switches the type of dentition to the previous type of dentition or the next type of dentition based on the tilt direction of the three-dimensional scanner. Thereby, it is possible for the user to switch to the desired type of dentition with one-time operation. Therefore, the three-dimensional scanner 100A according to the fourth embodiment has an effect of improving usability in addition to the effects of the three-dimensional scanner 100 according to the third embodiment.

Fifth Embodiment

In the first to fourth embodiments, the control table for the control unit 35 is only one and fixed. In contrast, in the fifth embodiment, a plurality of control tables are provided for the control unit, and the control tables may be switched to each other. In the fifth embodiment, there are provided a control table when the three-dimensional scanner is in an upright state and a control table when the three-dimensional scanner is tilted. Since the configuration of the three-dimensional scanner according to the fifth embodiment is the same as the configuration of the three-dimensional scanner 100A according to the fourth embodiment, the same components are denoted by the same reference numerals, and the description thereof will not be repeated.

Figures 12, 13A, 13B:
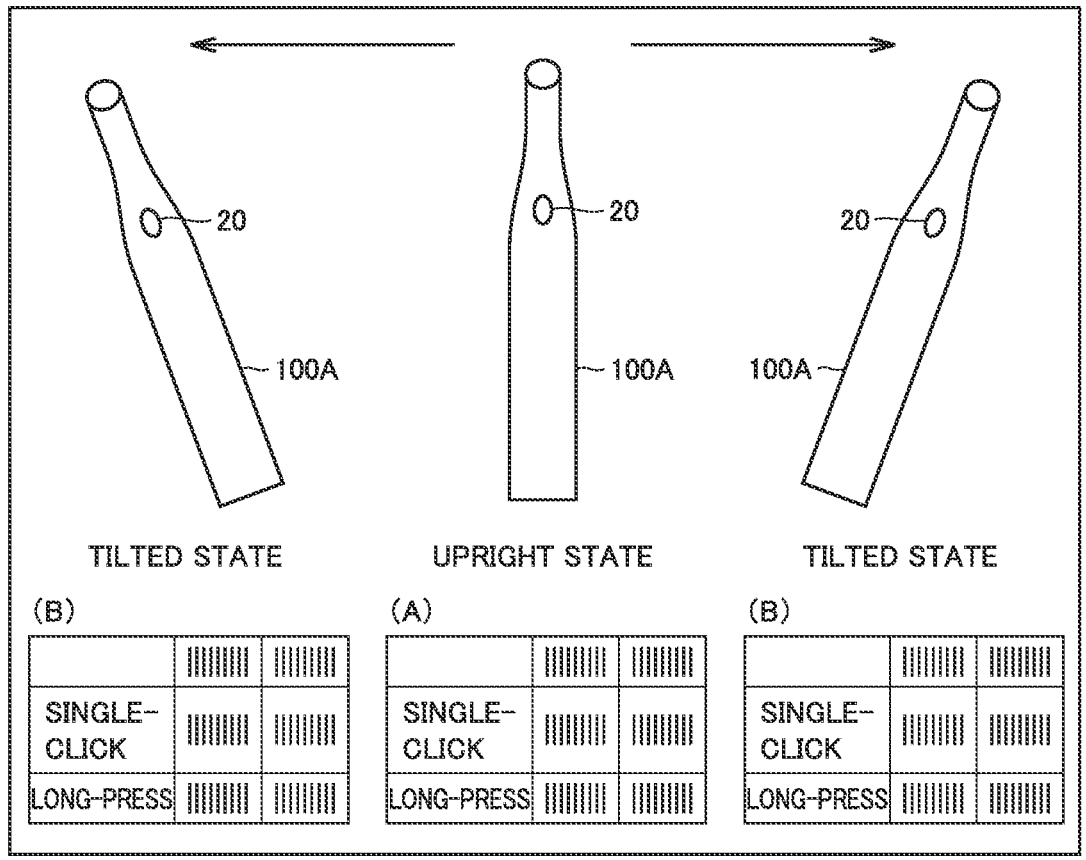
FIG. 12 is a diagram illustrating operations performed by a user according to a fifth embodiment.
FIG. 13A is a diagram illustrating a control table for the control unit when the instrument is in the upright state according to the fifth embodiment.
FIG. 13B is a diagram illustrating a control table for the control unit when the instrument is in a tilted state according to the fifth embodiment.

FIG. 12 is a diagram illustrating operations by a user according to the fifth embodiment. FIG. 13A is a diagram illustrating a control table for the control unit when the instrument is in the upright state according to the fifth embodiment. FIG. 13B is a diagram illustrating a control table for the control unit when the instrument is in a tilted state according to the fifth embodiment. When the user is long-pressing the reception unit 20 and the three-dimensional scanner 100A is in the upright state, the control unit 35 controls the imaging unit 30 based on the control table illustrated in FIG. 13A. On the contrary, when the user is long-pressing the reception unit 20 and the three-dimensional scanner 100A is in a tilted state, the control unit 35 controls the imaging unit 30 based on the control table illustrated in FIG. 13B.

With reference to FIGS. 13A and 13B, regardless of whether or not the three-dimensional scanner 100A is tilted, when the reception unit 20 receives a single-click operation from the user during the standby mode, the control unit 35 switches the standby mode to the scan mode. Thus, the scanning is started. On the contrary, regardless of whether or not the three-dimensional scanner 100A is tilted, when the reception unit 20 receives a single-click operation from the user during the scan mode, the control unit 35 switches the scan mode to the standby mode. Thus, the scanning is stopped. As described above, the user may switch between the standby mode and the scan mode simply by performing a single-click operation on the reception unit 20 regardless of whether or not the three-dimensional scanner 100A is tilted.

With reference to FIG. 13A, when the three-dimensional scanner 100A is in the upright state and is in the standby mode, if the reception unit 20 receives a long-press operation from the user, the control unit 35 changes the type of dentition. On the contrary, when the three-dimensional scanner 100A is in the upright state and is in the scan mode, if the reception unit 20 receives a long-press operation from the user, the control unit 35 changes the resolution. Changing the resolution means increasing the density of image data in the X and Y coordinates when the image is a two-dimensional image, and further increasing the density of image data in the Z coordinate when the image is a three-dimensional image.

With reference to FIG. 13B, when the three-dimensional scanner 100A is in a tilted state and is in the standby mode, if the reception unit 20 receives a long-press operation from the user, the control unit 35 switches between the color mode and the monochrome mode. On the contrary, when the three-dimensional scanner 100A is in a tilted state and is in the scan mode, if the reception unit 20 receives a long-press operation from the user, the control unit 35 switches the imaging mode to the snapshot mode.

FIG. 14 is a flowchart illustrating a process performed by the control unit 35 according to the fifth embodiment. The process is performed by the control unit 35 so as to achieve the controls illustrated in FIGS. 13A and 13B, and is realized by the CPU 36 executing a predetermined program stored in the ROM 37.

First, the control unit 35 determines whether or not a single-click operation is received by the reception unit 20 (step S51). If a single-click operation is received by the reception unit 20 (YES in step S51), the control unit 35 proceeds the process to step S52. On the contrary, if the single-click operation is not received by the reception unit 20 (NO in step S51), the control unit 35 proceeds the process to step S55.

In step S52, the control unit 35 determines whether or not the current mode is the scan mode. If the current mode is the scan mode (YES in step S52), the control unit 35 switches the scan mode to the standby mode (step S53), and ends the process illustrated in FIG. 14. On the contrary, if the current mode is not the scan mode, in other words, if the current mode is the standby mode (NO in step S52), the control unit 35 switches the standby mode to the scan mode (step S54), and returns the process to step S51.

In step S55, the control unit 35 determines whether or not a long-press operation is received by the reception unit 20. If a long-press operation is received by the reception unit 20 (YES in step S55), the control unit 35 proceeds the process to step S56. On the contrary, if a long-press operation is not received by the reception unit 20 (NO in step S55), the control unit 35 returns the process to step S51.

In step S56, the control unit 35 determines whether or not the current mode is the scan mode. If the current mode is the scan mode (YES in step S56), the control unit 35 proceeds the process to step S57. On the contrary, if the current mode is not the scan mode, in other words, if the current mode is the standby mode (NO in step S56), the control unit 35 proceeds the process to step S60.

In step S57, the control unit 35 determines whether or not the three-dimensional scanner 100A is in the upright state. If the three-dimensional scanner 100A is in the upright state (YES in step S57), the control unit 35 changes the resolution (step S58), and returns the process to step S51. On the contrary, if the three-dimensional scanner 100A is not in the upright state, in other words, if the three-dimensional scanner 100A is tilted (NO in step S57), the control unit 35 switches the scan mode to the snapshot mode (step S59), and returns the process to step S51.

In step S60, the control unit 35 determines whether or not the three-dimensional scanner 100A is in the upright state. If the three-dimensional scanner 100A is in the upright state (YES in step S60), the control unit 35 changes the type of dentition (step S61), and ends the process illustrated in FIG. 14. On the contrary, if the three-dimensional scanner 100A is not in the upright state, in other words, if the three-dimensional scanner 100A is tilted (NO in step S60), the control unit 35 switches between the color mode and the monochrome mode (step S62), and ends the process illustrated in FIG. 14.

As described above, the three-dimensional scanner 100A according to the fifth embodiment includes a casing 10 provided with a holding portion to be held by the user, a reception unit 20 provided on the casing 10 to receive an operation from the user, a control unit 35 that controls the imaging unit 30 to perform a predetermined action in response to the operation received by the reception unit 20, and a motion sensor 40 that detects the motion of the three-dimensional scanner 100A. Regardless of whether or not the three-dimensional scanner 100A is tilted, the control unit 35 switches between the scan mode and the standby mode when the reception unit 20 receives a single-click operation from the user. Further, when the three-dimensional scanner 100A is in the upright state and the reception unit 20 receives a long-press operation from the user during the standby mode, the control unit 35 changes the type of dentition; and when the three-dimensional scanner 100A is in the upright state and the reception unit 20 receives a long-press operation from the user during the scan mode, the control unit 35 changes the resolution. Furthermore, when the three-dimensional scanner 100A is tilted and the reception unit 20 receives a long-press operation from the user during the standby mode, the control unit 35 switches between the color mode and the monochrome mode; and when the three-dimensional scanner 100A is tilted and the reception unit 20 receives a long-press operation from the user during the scan mode, the control unit 35 changes the imaging mode to the snapshot mode.

Accordingly, in the fifth embodiment, the user may change the type of dentition or the imaging mode by long-pressing the reception unit 20 that is used for switching between the standby mode and the scan mode, and tilting the three-dimensional scanner 100A as necessary. In other words, the user may change the type of dentition or the imaging mode without touching the peripheral devices such as the mouse and the display unit 50, which prevents the contamination of bacteria, and thereby achieves sanitation.

In addition, in the fifth embodiment, the user does not need to touch the peripheral devices such as a mouse and the display unit 50 when changing the type of dentition or changing the imaging mode, and therefore there is no need to prepare a disposable glove or cover for operating the peripheral devices, which contributes to low cost and resource saving. In addition, since it is not necessary to wear a disposable glove or cover at the time of changing the type of dentition or changing the imaging mode, it is possible to improve usability and work efficiency for the user.

Further, in the fifth embodiment, based on a combination of an operation (for example, a long-press operation) performed by the user on the reception unit 20 that is used for switching between the standby mode and the scan mode, whether or not the current mode is the scan mode and the motion of the three-dimensional scanner 100A, a maximum number of 4 different controls (such as changing the type of dentition, changing the resolution, switching between the color mode and the monochrome mode and switching to the snapshot mode) can be performed. In other words, a small number of the reception unit 20 may be used to perform various controls, which makes it possible to reduce cost and improve usability.

Furthermore, in the fifth embodiment, the switching of the type of dentition, which is inevitably performed when imaging the teeth in the oral cavity, can be quickly done at the user's hand, which contributes to a reduction in imaging time so as to improve the user's work efficiency and reduce the burden on the patient.

In the fifth embodiment, only one reception unit 20 is provided on the casing 10, it is also acceptable to provide a plurality of reception units 20. For example, the casing 10 may be provided with a reception unit that is used for switching between the scan mode and the standby mode and a reception unit that is used for changing the type of dentition or changing the imaging mode. However, in consideration of cost and usability, it is preferred that the number of reception units 20 is as small as possible.

Further, in the fifth embodiment, the controls performed in response to the user's operation on the reception unit 20 are described as switching between the scan mode and the standby mode, changing the type of dentition, changing the resolution, switching between the color mode and the monochrome mode, and switching to the snapshot mode, but are not limited thereto. The controls performed in response to the user's operation on the reception unit 20 may include confirming the three-dimensional shape, rewinding scanned images, deleting a scanned image, replacing upper jaw image data with lower jaw image data or vice versa, or selecting an anchor tooth. Further, the user may arbitrarily select and set the contents of a control to be performed in response to a user's operation on the reception unit 20.

Furthermore, in the fifth embodiment, the control tables for the control unit 35 include 2 tables: a control table when the three-dimensional scanner 100A is in the upright state and a control table when the three-dimensional scanner 100A is in a tilted state. However, the control tables may be three or more. When the control tables for the control unit 35 are three or more, different control table may be used, for example, depending on the inclination angle of the three-dimensional scanner 100A.

Although the embodiments of the present invention have been described, it should be understood that the embodiments disclosed herein have been presented for the purpose of illustration and description but not limited in all aspects. It is intended that the scope of the present invention is not limited to the description above but defined by the scope of the claims and encompasses all modifications equivalent in meaning and scope to the claims.

What is claimed is:

1. A handheld dental instrument comprising:
a casing provided with a holding portion to be held by a user;
a reception unit provided on the casing to receive an operation from the user; and
a control unit that controls a control target to perform a predetermined action in response to the operation received by the reception unit,
the control unit performing a first control when the operation received by the reception unit from the user is a first operation, and performing a second control different from the first control when the operation received by the reception unit from the user is a second operation different from the first operation,
wherein when the operation received by the reception unit from the user is the first operation in the first control, the control unit switches between a first mode and a second mode,
the second control performed when the operation received by the reception unit from the user in the first mode is the second operation is different in control contents from the second control performed when the operation received by the reception unit from the user in the second mode is the second operation.

2. The dental instrument according to claim 1, wherein the control target is an imaging unit that captures an image of a tooth in the oral cavity,
the first mode is an imaging mode in which a tooth in the oral cavity is allowed to be imaged, and
the second mode is a standby mode in which a tooth in the oral cavity is not allowed to be imaged.

3. The dental instrument according to claim 2, wherein in the imaging mode, the imaging unit is allowed to continuously capture images of a plurality of teeth so as to generate a dentition image based on the images of the plurality of teeth, and when the operation received by the reception unit from the user is the first operation, the imaging mode is switched to the standby mode, and
in the standby mode, the imaging unit is not allowed to continuously capture images of a plurality of teeth, and when the operation received by the reception unit from the user is the first operation, the standby mode is switched to the imaging mode.

4. The dental instrument according to claim 2, wherein the control unit performs the second control to change an imaging mode when the operation received by the reception unit from the user in the imaging mode is the second operation.

5. The dental instrument according to claim 3, wherein the control unit performs the second control to change a type of the dentition image to be generated in the imaging mode when the operation received by the reception unit from the user in the standby mode is the second operation.

6. The dental instrument according to claim 1, further comprising
a detection unit that detects the motion of the dental instrument, wherein the control unit performs a change operation on the second control in response to the motion detected by the detection unit.

7. The dental instrument according to claim 1, further comprising a detection unit that detects the motion of the dental instrument, wherein
the control unit varies the control contents of the second control in the first mode and the second mode in response to the motion detected by the detection unit.

8. The dental instrument according to claim 1, wherein the reception unit is one of a single button, a single touch sensor, and a single dial.

9. The dental instrument according to claim 1, wherein the first operation is a single operation performed in a predetermined period, and the second operation is a multiple operation performed in the predetermined period.

10. The dental instrument according to claim 9, wherein the multiple operation includes a case where the single operation is repeatedly performed for a plurality of times in the predetermined period or a case where the single operation is continued in the predetermined period.

11. The dental instrument according to claim 1, wherein the dental instrument is a three-dimensional scanner that measures a three-dimensional shape of teeth in the oral cavity.

12. The dental instrument according to claim 1, wherein the control unit allows the user to arbitrarily set the control contents to be performed in response to the first operation and the control contents to be performed in response to the second operation.

13. A method of controlling a handheld dental instrument in response to an operation from a user,
the handheld dental instrument including:
  a casing provided with a holding portion to be held by the user;
  a reception unit provided on the casing to receive an operation from the user; and
  a control unit that controls a control target to perform a predetermined action in response to the operation received by the reception unit,
the control method including:
  performing a first control when the operation received by the reception unit from the user is a first operation, wherein when the operation received by the reception unit from the user is the first operation in the first control, the control unit switches between a first mode and a second mode; and
  performing a second control different from the first control when the operation received by the reception unit from the user is a second operation different from the first operation wherein the second control performed when the operation received by the reception unit from the user in the first mode is the second operation is different in control contents from the second control performed when the operation received by the reception unit from the user in the second mode is the second operation.

14. A handheld three-dimensional measuring device that performs a three-dimensional measurement on an object in the oral cavity, the three-dimensional measuring device comprising:
  a casing provided with a holding portion to be held by a user;
  a reception unit provided on the casing to receive an operation from the user; and
  a control unit that performs the three-dimensional measurement in response to the operation received by the reception unit,
  when the three-dimensional measurement is not performed, the control unit performing the three-dimensional measurement if the operation received by the reception unit from the user is a simple operation,
  when the three-dimensional measurement is being performed, the control unit stopping the three-dimensional measurement if the operation received by the reception unit from the user is the simple operation, and
  if the operation received by the reception unit from the user is a complicated operation that is more complicated than the simple operation, the control unit at least changing the amount of data to be obtained by the three-dimensional measurement, changing the quality of an image to be generated based on data to be obtained by the three-dimensional measurement, changing a method of performing the three-dimensional measurement, and/or generating an image of the object during the three-dimensional measurement.

* * * * *